(12) United States Patent
McCarthy et al.

(10) Patent No.: US 6,410,315 B1
(45) Date of Patent: Jun. 25, 2002

(54) GENES ENCODING POLYPEPTIDES CONTAINING SIGNAL SEQUENCES

(75) Inventors: Sean A. McCarthy, Boston; Steven Bossone, Lexington, both of MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/436,183

(22) Filed: Nov. 8, 1999

Related U.S. Application Data (62) Division of application No. 08/966,269, filed on Nov. 7, 1997, now Pat. No. 6,046,000.

(51) Int. Cl.[7] .......................... C12N 15/63; C12N 5/00; C07H 21/04
(52) U.S. Cl. .................... 435/320.1; 435/425; 536/23.1
(58) Field of Search .............................. 435/320.1, 425; 536/23.1

(56) References Cited

U.S. PATENT DOCUMENTS

| | | | |
|---|---|---|---|
| 5,395,922 A | 3/1995 | Bjorn et al. | 530/350 |
| 5,525,486 A | 6/1996 | Honjo et al. | 435/69.1 |
| 5,536,637 A | 7/1996 | Jacobs | 435/6 |
| 5,665,590 A | 9/1997 | Yang | 435/6 |
| 5,712,116 A | 1/1998 | Jacobs | 435/69.1 |
| 5,753,462 A | 5/1998 | Lok | 435/6 |

FOREIGN PATENT DOCUMENTS

| EP | 0 670 369 | 6/1995 |
|---|---|---|

OTHER PUBLICATIONS

Hillier et al. Genome Res. vol. 6(9):807–828, Sep. 1996.*
Brown et al., "SKN7, a Yeast Multicopy Suppressor of a Mutation Affecting Cell Wall B–Glucan Assembly . . . " J. of Bacteriology 175(21):6908–6915, 1993.
Brown et al., "The Yeast KRE9 Gene Encodes an O Glycoprotein Involved in Cell Surface B–Glucan Assembly" Mol. and Cell. Biol. 13(10):6346–6356, 1993.
Dijkgraaf et al., "The KNH1 Gene of Saccharomyces cerevisiae is a Funtional Homolog of KRE9" Yeast 12:683–692, 1996.
Klein et al., "Selection for genes encoding secreted proteins and receptors" Proc. Natl. Acad. Sci. USA 93:7108–7113, 1996.
Nielsen et al., "Identification of prokaryotic and eukaryotic signal peptides and prediction of their cleavage sites" Protein Engineering 10(1):1–6, 1997.
Tashiro et al., "Signal Sequence Trap: A Cloning Strategy for Secreted Proteins and Type I Membrane proteins" Science 261:600–603, 1993.

* cited by examiner

Primary Examiner—Terry McKelvey
Assistant Examiner—William Sandals
(74) Attorney, Agent, or Firm—Millennium Pharmaceuticals, Inc.

(57) ABSTRACT

The invention involves a method of identifying nucleic acid sequences encoding signal peptide-containing proteins. The method features chimeric constructs containing a KRE9 gene that lacks a signal sequence. Yeast containing chimeric KRE9 plasmid constructs that encode signal sequences are selected based on their ability to grow on media in which sucrose is the sole carbon source.

14 Claims, 5 Drawing Sheets

```
GGGGACCGTGTTTGTGGCCCCAAGCCGGTGCCCCCATTTTGGAACTCAGCGAGTAGGGGGGCTCTGGGAAGTGG    79

CAGGGGGCAGCAGCTGCTGCCTCCACTTCCCTAGCCAGGTGCTGAAGAGGATCTTCGGAGCCGCTCTGGCCCCAGG   158

CGCTGGATGACTGGCACCAGCGCTCCTCGCACCTGTGTTGGTGTGTGAGACTTGGGCTGGAGTGCCCACGTGGCTGTGG   237

AGTCAGTGTGATTCATGATTGAGGAAACGCGTCCTCCCATCCTCTCTCCTTGGCACTTTCCACACATGAGGAGAAGAA   316

M   K   G   T   C   V   I      7
GAGCTTCTGTTTAGAAGACACGTGCCCAGAGTCAGCCCCTGCCCACC ATG AAG GGA ACC TGT GTT ATA    388

A   W   L   F   S   S   L   G   L   W   R   L   A   H   P   E   A   Q   G   T     27
GCA TGG CTG TTC TCA AGC CTG GGG CTG TGG AGA CTC GCC CAC CCA GAG GCC CAG GGT ACG   448

T   Q   C   Q   R   T   L   E   V   N   I   V   S   P   S   S   K   A   T   F     47
ACT CAG TGC CAG AGA ACA CTC GAG GTG AAT ATT GTT TCC CCC AGC TCC AAG GCA ACA TTC   508

S   P   S    (SEQ ID NO:2)     50
AGT CCA AGT  (SEQ ID NO:1)     517
```

TTCTTCCTAGTTTCTTTTTCGGCACAATATATTCAAGTTATACCAAGCATACAATCAACTCCCAAGTTGGGATCCGAATT

M  R  S  L  L  R
     CGGCACGAGCGGCACGAGTTGTGCTTCGGAGACCGTAAGGATATATTGATGACC ATG AGA TCC CTG CTC AGA

T   P   F   L   C   G   L   L   W   A   F   C   A   P   G   A   R   A   E   E
     ACC CCC TTC CTG TGT GGC CTG CTC TGG GCC TTT TGT GCC CCA GGC GCC AGG GCT GAG GAG

P   A   A   S   F   S   Q   P   G   S   M   G   L   D   K   N   T   V   H   D
     CCT GCA GCC AGC TTC TCC CAA CCC GGC AGC ATG GGC CTG GAT AAG AAC ACA GTG CAC GAC

Q   E   H   I   M   E   H   L   E   G   V   I   N   K   P   E   A   E   M   S
     CAA GAG CAT ATC ATG GAG CAT CTA GAG GGT GTC ATC AAC AAA CCA GAG GCG GAG ATG TCG

P   Q   E   L   Q   L   Y   F   K   M   H   D   Y   D   G   N   N   L   L
     CCA CAA GAA TTG CAG CTC CAG CAT TAC TTC AAA ATG CAT GAT TAT GAT GGC AAT AAT TTG CTT

D   G   L   E   L   S   T   A   I   T   H   V   H   K   E   G   S   E   Q
     GAT GGC TTA GAA CTC TCC ACA GCC ATC ACT CAT GTC CAT AAG GAG GGG AGT GAA CAG

A   P   L   E   V   N   I   V   S   P   S   S   K   A   T   F   S   P   S
     GCA CCA CTC GAG GTG AAT ATT GTT TCC CCC AGC TCC AAG GCA ACA TTC AGT CCA AGT (SEQ ID NO:4)
     (SEQ ID NO:3)
```

FIG. 3

Comparison of novel protein sequence emxosb4a11
to murine semaphorin F (Genbank Accession number X97817)

Identities = 22/32 (68%), Similarities = 26/32 (81%)

```
emxosb4a11:  1  MKGTCVIAWLFSSLGLWRLAHPEAQGTTQCQR  32
                MKG C+ +AWLFSSLG+WRLA PE Q   +CQR
mu semF:     1  MKGACILAWLFSSLGVWRLARPETQDPAKCQR  32
```

Underlined - predicted signal peptide

FIG. 4

Comparison of emxosb4f08 to probable calcium-binding protein (CaBP)
(Genbank Accession number JS0027)

```
emxosb4f08   1   MRSLLRTPFLCGLLWAFCAPGARAEEPAASFSQPGSMGLDKN        42 emxosb4f08  43   TVHDQEHIMEHLEGVINKEAEMSPQELQLHYFKMHDYDGNNL        84
                                 MSPQELQLHYFKMHDYDGNNL
CaBP         1                   MSPQELQLHYFKMHDYDGNNL        21 emxosb4f08  85   LDGLELSTAITHVHKEEGSEQAPL                         109
                 LDGLELSTAITHVHKEEGSEQAPL
CaBP        22   LDGLELSTAITHVHKEEGSEQAPL                          45
```

Underlined - predicted signal peptide

FIG. 5

GENES ENCODING POLYPEPTIDES CONTAINING SIGNAL SEQUENCES

RELATED APPLICATION INFORMATION

This application is a divisional of application Ser. No. 08/966,269, filed Nov. 7, 1997 now U.S. Pat. No. 6,046,000.

BACKGROUND OF THE INVENTION

The invention relates to methods for identifying genes encoding signal sequences.

The demonstrated clinical utility of certain growth factors and cytokines, for example, insulin, erythropoietin, granulocyte-colony stimulating factor, granulocyte-macrophage colony stimulating factor, human growth hormone, interferon-beta, and interleukin-2 in the treatment of human disease has generated considerable interest in identifying novel proteins of this class.

Since growth factors and cytokines are secreted proteins, they often possess "signal sequences" at their amino terminal end. The signal sequence directs a secreted or membrane protein to a sub-cellular membrane compartment, the endoplasmic reticulum, from which the protein is dispatched for secretion from the cell or presentation on the cell surface. Techniques that detect signal sequences or nucleic acid sequences encoding a signal sequence have been employed as tools in the discovery of novel cytokines and growth factors.

Among the methods that have been used to identify secreted proteins are methods that rely on the homology between some secreted proteins. For example, DNA probes or PCR oligonucleotides that recognize sequence motifs present in genes encoding known secreted proteins have been used in screening assays to identify novel secreted proteins. In a related approach, homology-directed sequence searching of Expressed Sequence Tag (EST) sequences generated by high-throughput sequencing of specific cDNA libraries has been used to identify genes encoding secreted proteins. Both of these approaches can identify a signal sequence when there is a high degree of similarity between the DNA sequence used as a probe and the putative signal sequence.

"Signal peptide trapping" has also been used to identify secreted proteins (Tashiro et al., 1993, Science 261:600–603; Honjo et al., 1996; U.S. Pat. No. 5,525,486, and U.S. Pat. No. 5,536,637). Generically, this technique involves the ligation of cDNA, prepared from various mRNA sources, to a reporter gene lacking a signal sequence. The resulting chimeric constructs are introduced into an appropriate host cell. Depending upon the nature of the reporter gene, host cells are scored for either the presence of reporter protein at the cell surface or secretion of the reporter protein from cells. In both cases, a positive score indicates that the cell harbors a chimeric construct having a cDNA encoding a signal sequence which directs the export of the reporter protein to the cell surface or into the extracellular medium.

In a related method (Klein et al., 1996, Proc. Nat. Acad. Sci. USA 93:7108–7113; Jacobs, 1996, U.S. Pat. No. 5,536,637) the Saccharomyces cerevisiae gene, SUC2, which encodes a secreted invertase protein, is used as a reporter. Invertase catalyzes the hydrolysis of sucrose into glucose and fructose, sugars which, unlike sucrose, can be readily utilized by S. cerevisiae as a carbon source. Strains of S. cerevisiae that cannot secrete SUC2 protein are unable to grow on media with sucrose as the sole carbon source. Thus, a mutant SUC2 gene which does not encode a signal peptide can be used as a reporter in signal sequence trapping. Chimeric constructs composed of random cDNAs fused to DNA encoding SUC2 lacking a signal sequence are transformed into S. cerevisiae, and transformants secreting chimeric SUC2 are selected by growing the transformants under conditions where sucrose is the sole carbon source. This method offers a genetic selection for cDNAs encoding signal peptides.

SUMMARY OF THE INVENTION

The invention features a method for identifying nucleic acid sequences encoding signal sequences. Most secreted and membrane-associated proteins possess such signal sequences composed of 15–30 hydrophobic amino acid residues at their amino termini. Because signal sequences are present in secreted proteins and membrane-associated proteins, the identified nucleic acid sequences, which will encode at least a portion of a secreted or membrane-associated protein, can be used to isolate additional nucleic acid molecules encoding the entirety of the secreted or membrane-associated protein.

KRE9 is an example of a yeast secreted protein. Yeast KRE9 null mutants show severe growth retardation (essentially no growth) when glucose is the sole carbon source. Growth of a KRE9 null mutant on glucose can be restored by transformation with DNA encoding wild type KRE9 protein, but not by transformation with DNA encoding a mutant KRE9 protein lacking a signal sequence. Thus, secretion of KRE9 protein via its signal sequence is required for its normal function. Importantly, the presence of extracellular KRE9 protein does not rescue the KRE9 null phenotype. This result suggests that KRE9 protein must pass through the secretory pathway in order to exert its normal function. Although yeast KRE9 null mutants show essentially no growth when glucose is used as the carbon source, they can be maintained on galactose because of induction of the KNH1, a functional homolog of KRE9.

The invention features a method for identifying secreted and membrane-associated proteins using yeast that lack functional KRE9 protein and are transformed with a chimeric DNA molecule in which a mutant KRE9 gene lacking its signal sequence encoding portion is fused to a test sequence. The transformed yeast are grown on a selective medium that is designed permit (or prevent) growth of cells which produce functional, secreted KRE9. If the test sequence encodes a signal sequence (fused in-frame to the sequence encoding mature KRE9 protein), the yeast cell will grow (or not grow in the case of a selective medium which is designed to prevent growth of cells expressing functional, secreted KRE9) on the selective medium. Thus, the invention features a novel selection method utilizing DNA constructs containing a chimeric KRE9 gene in which the part of the KRE9 gene encoding the native KRE9 signal sequence is replaced with a candidate signal sequence encoding sequence. The ability of these chimeric constructs to rescue KRE9 null mutants grown on glucose is tested as follows. The chimeric constructs are used to transform KRE9 null mutants. The transformed cells are transferred to plates having glucose as the sole carbon source. Those chimeric constructs that allow a transformed KRE9 null mutant to grow on glucose contain candidate signal sequence encoding sequences.

Since growth factors and cytokines are secreted proteins, possessing signal sequences at their amino termini, signal sequence trapping can be employed as a tool in the discovery of novel proteins of this class.

One embodiment of the methods of the invention includes the following steps:
(a) obtaining a nucleic acid molecule which includes a chimeric gene, the chimeric gene including a first portion and a second portion, the first portion encoding a KRE9 lacking a functional signal sequence and the second portion being a heterologous nucleic acid sequence;
(b) transforming a yeast cell lacking a functional KRE9 gene with the nucleic acid molecule; and
(c) determining whether the transformed yeast cell grows when supplied with a medium that permits growth of a yeast cell expressing KRE9 having a functional signal sequence, but does not permit growth of a yeast cell that does not express KRE9 having a functional signal sequence, wherein growth on the medium indicates that the heterologous nucleic acid sequence present in the yeast cell encodes a signal sequence.

In another embodiment the method, step (a) includes:
(i) obtaining double-stranded DNA; and
(ii) ligating the double-stranded DNA to a DNA molecule encoding KRE9 lacking a functional signal sequence to create a chimeric gene.

In another embodiment of the invention step (a) includes:
(i) obtaining double-stranded DNA;
(ii) ligating the double-stranded DNA to a DNA molecule encoding KRE9 lacking a functional signal sequence to create a chimeric gene;
(iii) transforming a bacterium with a nucleic acid molecule that includes the chimeric gene;
(iv) growing the transformed bacterium; and
(v) isolating the nucleic acid molecule which includes the a chimeric gene from the transformed bacterium.

In another embodiment of the invention the method, in order to identify the signal sequence, the method includes: isolating and sequencing a portion of the chimeric gene contained within a yeast cell that grows when supplied with a medium that permits growth of a yeast cell expressing KRE9, but does not permit growth of a yeast cell that does not express KRE9 having a functional signal sequence.

In various preferred embodiments, first portion of the nucleic acid molecule is pBOSS1; second portion of the nucleic acid molecule is cDNA; the yeast strain is Yscreen2; the medium contains glucose as the sole carbon source; the medium contains a calcineurin inhibitor; and the method includes using a nucleic acid molecule encoding the signal sequence to screen an eukaryotic library for a full-length gene or cDNA encoding a protein comprising the identified signal sequence.

The invention also features a yeast cell transformed with a nucleic acid molecule comprising a chimeric gene, the chimeric gene comprising a first portion and a second portion, the first portion encoding a KRE9 lacking a functional signal sequence and the second portion being a heterologous nucleic acid sequence.

The invention also features a method that includes:
(a) obtaining a nucleic acid molecule which includes a chimeric gene, the chimeric gene including a first portion and a second portion, the first portion encoding a KRE9 lacking a functional signal sequence and the second portion being a heterologous nucleic acid sequence;
(b) transforming a yeast cell lacking a functional KRE9 gene with the nucleic acid molecule; and
(c) determining whether the transformed yeast cell grows when supplied with a medium that does not permit growth of a yeast cell expressing KRE9 having a functional signal sequence, but does permit growth of a yeast cell that does not express KRE9 having a functional signal sequence, wherein lack of growth on the medium indicates that the heterologous nucleic acid sequence present in the yeast cell encodes a signal sequence. In a preferred embodiment the medium contains K1 killer toxin.

In another preferred embodiment step (a) includes: (i) obtaining a double-stranded DNA; and (ii) ligating the double-stranded DNA to a DNA molecule encoding KRE9 lacking a functional signal sequence to create a chimeric gene.

In a another preferred embodiment the method, in order to identify the signal sequence, includes: isolating and sequencing a portion of the chimeric gene contained within the yeast cell that does not grow when supplied with a medium that does not permit growth of a yeast cell expressing KRE9, but does permit growth of a yeast cell that does not express KRE9 having a functional signal sequence.

The invention also features the expression vector pBOSS-1 and a genetically engineered host cell which harbors pBOSS-1.

A "nonfunctional KRE9 gene" is a KRE9 gene having a mutation or deletion in its signal sequence encoding portion such that the gene does not encode a functional signal sequence and thus does not produce a functional KRE9 protein. Cells which fail to produce functional KRE9 protein exhibit slow vegetative growth and are effectively unable to grow on glucose. In the case where the nonfunctional KRE9 gene is produced by a point mutation, it is preferable that there be more than one mutation to decrease the chance of reversion to the wild type.

The KRE9-based signal sequence trap of the invention includes a positive selection method to screen for putative signal sequence encoding sequences. The selection strategy permits screening of a large number putative signal sequence encoding sequences because those cells that do not contain such a sequence essentially do not grow. This is in contrast to most other signal trap methods such as that described in U.S. Pat. No. 5,525,486 which rely solely on the detection of a protein encoded by a reporter gene. Furthermore, because there is no cross-feeding, a relatively large number of yeast can screened on any given plate.

In an alternative selection method of the invention, a negative selection is employed using K1 killer toxin. K1 killer toxin appears to kill sensitive yeast cells following binding to cell wall β1,6-glucans. Thus, cells with mutations in KRE9 are resistant to killing by K1 killer toxin. This selection method confers advantages similar those of the positive selection strategy in that large numbers of putative signal sequence encoding sequences can be screened.

Without being bound by any particular theory, the KRE9 protein reportedly encodes a soluble secretory-pathway protein required for yeast cell wall synthesis and growth. Specifically, the KRE9 protein plays a significant role in synthesis of cell surface β1,6-glucan (Brown and Bussey, 1993, Mol. Cell. Biol. 13:6346–6356) which is necessary for normal cell growth. When glucose is present in the medium, β1,6-glucan synthesis is normal provided that functional, secreted KRE9 protein is present. In the absence of functional KRE9 protein, yeast cells grow slowly when glucose is provided in the medium because of abnormal cell wall synthesis.

The KRE9-based signal trap, which is based on biosynthetic requirements, contrasts with the principle of signal trap systems based on catabolic requirements, for example the SUC2 signal trap selection system (U.S. Pat. No. 5,536, 637). SUC2 protein is involved in catabolism in that it cleaves certain sugars to form nutrients which can be used as a carbon and energy source. As described above, the SUC2 signal trap selection system is based on the fact that yeast cells that lack functional SUC2 protein cannot utilize sucrose or raffinose as a carbon source. Thus, SUC2 null cells cannot grow when sucrose or raffinose is the sole carbon source.

One important advantage of a KRE9-based signal sequence trap of the invention is the low number of false positives generated by this method. This is in contrast to other signal trap methods such as that based on the yeast SUC2(U.S. Pat. No. 5,536,637). SUC2 null mutants are unable to grow when the energy source is sucrose or raffinose. When presented extracellularly, SUC2 protein can rescue SUC2 null mutants grown under restrictive conditions via a phenomenon referred to as cross-feeding. This arises because extracellular SUC2 protein cleaves sucrose into diffusible nutrients on which neighboring yeast cells can grow (i.e., fructose and glucose). KRE9 null mutants are not subject to cross-feeding, because extracellular KRE9 cannot restore growth of null KRE9 mutants on glucose. Thus, a KRE9 gene engineered to lack its signal sequence can be used as a reporter in signal sequence trapping and will not be subject to the background problems (i.e., false positives) that limit can limit the success of the less tightly regulated selection systems. Because the method of the invention is not subject to background problems to any significant degree, higher throughput screening is possible.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DETAILED DESCRIPTION

The present invention capitalizes on the *S. cerevisiae* redundant gene pair, KRE9 and KNH1 in a method for identifying signal sequence encoding sequences and signal sequences. The KRE9 gene encodes a secreted protein, predicted to have a 21 amino acid signal peptide. The KRE9 protein is required for the synthesis of the yeast cell wall polymer (1→6)-β-glucan which makes up about half of the dry weight of the cell (Brown and Bussey, 1993, Mol. Cell. Biol. 13:6346–6356). Although KRE9 null strains grow very poorly on glucose (effectively there is no growth), these strains grow vigorously on galactose. This is probably due to the induction by galactose of the KNH1 gene, a functional homolog of the KRE9 gene with which it shares 46% identity (Dijkgraaf et al., 1996, Yeast 12:683–692). Thus, the KRE9 null strains that are an essential part of the invention can be maintained on galactose, and selection for strains containing functional KRE9 can be performed by selection on glucose.

KRE9 is used as a reporter in the signal sequence trap of the invention. To use KRE9 as a reporter in signal sequence trapping, a KRE9 null strain that is unable to grow under restrictive conditions (e.g., when glucose is the sole carbon source provided in the medium) must be used. An example of a suitable KRE9 null strain (Yscreen2) is described in Example 1. Other appropriate strains can be constructed using methods described in Example 1 and methods known to those in the art.

In one embodiment, the signal sequence trap of the invention involves ligating a cDNA to a mutant KRE9 gene that does not encode a signal sequence, thus creating a chimeric gene (Example 1). The chimeric gene is used to transform a yeast KRE9 null strain. The transformants are then grown under a selective condition (e.g., in medium containing glucose as the sole carbon source) that does not permit growth of yeast that are null for KRE9. Only those chimeric genes encoding a signal sequence can restore the function of KRE9 by facilitating its secretion, thus permitting growth under the selective condition (Example 2). This screening strategy offers a rapid and efficient direct growth selection for cDNAs encoding a signal sequence and, as mentioned above, avoids the problems of cross-feeding associated with the SUC2 method. The ability of this method to identify novel sequences is demonstrated in Example 3. Various additional embodiments of the invention are described in Examples 4–5.

In one embodiment, the method of the invention includes the following steps: a) obtain double-stranded cDNA from an eukaryotic cell and ligate the eukaryotic cDNA to an appropriate plasmid vector containing a mutant KRE9 gene that does not encode a signal sequence; then transform an *E. coli* with the ligated DNA, culture the transformed *E. coli*, and isolate plasmid DNA from the transformants; b) transform an *S. cerevisiae* KRE9 null mutant with the isolated plasmid DNA; and c) select transformed yeast strains encoding functional KRE9 fusion proteins by growth on a selective medium (e.g., glucose). The method can also include the following additional steps: isolate plasmid DNA from the selected yeast; transform *E. coli* with the isolated DNA; isolate plasmid DNA from the transformed *E. coli;* determine the nucleotide sequence of the heterologous DNA; and analyze sequences to identify novel secreted proteins.

A KRE9 nucleic acid for use in the invention can be obtained by cloning as described, for example in Brown and Bussey, 1993, supra. The sequence of KRE9 is described in several databases including GenBank (Accession No. Z49449x1) and Swiss-Prot (Accession No. P39005).

A yeast expression vector appropriate for use in the invention can be constructed as described below (Example 1, step 2) or from other suitable vectors. Examples of such vectors are described in, for example, Pouwels et al. (*Cloning Vectors*, Elsevier, N.Y., 1987 and Supplements); Rose et al., 1990, *Methods in Yeast Genetics: A Laboratory Course Manual*, Cold Spring Harbor Laboratory Press, Cold Spring Harbor, N.Y.; and Guthrie and Fink, eds., 1991, *Guide to Yeast Genetics and Molecular Biology*, Meth. Enzymol. 194, Academic Press, Inc. Harcourt, Brace Jovanovich, New York. An appropriate yeast expression vector for use in the invention includes a suitable yeast promoter and transcription terminator (e.g., those of alcohol dehydrogenase; ADH1), and a yeast origin of replication (e.g. the $2\mu$ origin). For those embodiments including a selection step in *E. coli*; at least an *E. coli* origin of replication, and one or more *E. coli* selectable markers such as drug resistance genes (e.g., genes conferring ampicillin, chloramphenicol, or tetracycline resistance) are generally included in the vector.

Although cDNA from any eukaryote can be used for the invention, in general, mammalian, preferably human cDNA is used. It is also possible to use genomic DNA instead of cDNA. Methods for inserting a nucleic acid such as a cDNA into a yeast expression vector (plasmid) used in the invention are known in the art; including methods for obtaining cDNA, ligation of heterologous nucleic acids, transformation of yeast and bacteria, isolation of plasmids, and DNA sequencing and analysis. The examples below describe acceptable methods for these procedures. Further guidance can be acquired from, for example, Ausubel et al., (*Current Protocols in Molecular Biology*, Green Publishing Associates, Inc., and John Wiley & Sons, Inc., NY, 1989), Sambrook et al. (*Molecular Cloning: A Laboratory Manual*, Cold Spring Harbor Laboratory Press, Cold Spring Harbor, N.Y., 1989), Guthrie and Fink (eds, *Methods in Yeast Genetics: A Laboratory Course Manual*, Cold Spring Harbor Laboratory Press, Cold Spring Harbor, N.Y., 1991), and *Guide to Yeast Genetics and Molecular Biology*, Meth. Enzymol. 194, Academic Press, Inc. Harcourt, Brace Jovanovich, New York).

Nucleic acid sequences encoding putative signal sequences can be analyzed using sequence analysis software such as the Sequence Analysis Software Package of the Genetics Computer Group, University of Wisconsin Biotechnology Center, 1710 University Avenue, Madison, Wis. 53705, with the default parameters as specified therein. Parameters of a putative signal sequence that can be measured using such software include the extent of homology to known sequences. The software package Signal P (Nielsen et al., 1997, Protein Engineering 10:1–6) can also be used to analyze a signal sequence.

The invention also encompasses screening cDNA or genomic libraries to obtain full-length cDNAs or genes using a nucleic acid encoding a signal sequence identified as described herein. Many such libraries are known in the art. Methods of constructing cDNA and genomic libraries are known in the art (for example, see Sambrook et al., 1989, supra; Ausubel et al., 1989, supra).

A library is screened by hybridizing nucleic acid molecules encoding sequences (identified as described above) to nucleic acid molecules in a library under stringent conditions. The sequence encoding a signal sequence can also be used to identify sequences encoding homologous polypeptides in other species. Accordingly, the invention includes methods of detecting and isolating these nucleic acid molecules. Using these methods, a sample (for example, a nucleic acid library, such as a cDNA or genomic library) is contacted (or "screened") with a probe encoding at least a portion of an identified signal sequence that is at least 25 or 50 nucleotides long. The probe selectively hybridizes to nucleic acids encoding related polypeptides (or to complementary sequences thereof). The term "selectively hybridize" is used to refer to an event in which a probe binds to nucleic acids encoding the signal sequence (or to complementary sequences thereof) to a detectably greater extent than to nucleic acids encoding other signal sequences (or to complementary sequences thereof). The probe, which can contain at least 25 (for example, 25, 50, 100, or 200 nucleotides) can be produced using any of several standard methods (see, for example, Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a signal sequence-specific nucleic acid sequence. The probes are used to screen a nucleic acid library, thereby detecting nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but also allows some non-specific interaction between less than perfectly matched sequences. After hybridization, the nucleic acids can be "washed" under conditions of moderate or high stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

Another example set of conditions that are considered "stringent conditions" are those in which hybridization is carried out at 50° C. in Church buffer (7% SDS, 0.5% NaHPO$_4$, 1 M EDTA, 1% BSA), and washing is carried out at 50° C. in 2×SSC.

Once detected, the nucleic acid molecules can be isolated and sequenced by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

Although ΔKRE9 function can be restored by heterologous mammalian signal sequences, it is not clear whether all N-terminal protein fusions of secreted proteins with ΔKRE9 will regain appropriate function. For example, fusion of KRE9 to a large portion of another protein may interfere with KRE9 function even under circumstances which permit secretion of the fusion protein. This issue is addressed by the inclusion of a sequence encoding a cleavage site for the KEX2 protease (lysine-arginine-aspartic acid; Julius et al., 1984, Cell 37:1075) at the junction between the mammalian cDNAs and the ΔKRE9 cDNA in the nucleic acid molecule of the invention (e.g., in the chimeric gene of the invention in pBOSS1). KEX2 can cleave the fusion protein as it passes through the cellular secretory apparatus, thus relieving ΔKRE9 of any functional impairment imposed by the N-terminal fusion.

EXAMPLES

The following examples illustrate the invention, including constructing an appropriate yeast strain and vector, and selective conditions useful for identifying a vector containing a sequence encoding a signal sequence.

Example 1

Construction of a Signal Trap Screening System
Step 1: Strain Development

The first step in developing the KRE9-based signal peptide trapping system was construction of an appropriate yeast strain. Standard media and techniques appropriate for Saccharomyces were used (Rose et al., 1990, *Methods in Yeast Genetics: A Laboratory Course Manual*, Cold Spring Harbor Laboratory Press, Cold Spring Harbor, N.Y.; Guthrie and Fink, eds., 1991, *Guide to Yeast Genetics and Molecular Biology*, Meth. Enzymol. 194, Academic Press, Inc. Harcourt, Brace Jovanovich, New York). The parent strain used for the construction was the haploid SEY 6210/ kre9::HIS (mat a, leu2-3, ura3-52, his3-Δ200, lys2-801, trp-Δ901, suc2-Ä9) containing wild type KRE9 on a PRS 316/URA3 vector (Yscreen1; Brown and Bussey, 1993). This strain is maintained on SD/-his,-ura (1.7 g yeast nitrogen base without amino acids and ammonium sulphate (DIFCO), 5 g ammonium sulfate, 0.66 g -His/-Ura dropout powder (Clontech; Palo Alto, Calif.), 20 g dextrose, and 20 g BACTO-AGAR® brand solidifying agent per liter).

Yscreen1 was further engineered to lose the PRS 316-KRE9Δ containing plasmid, thereby creating a true KRE9 null strain. This was accomplished by plating Yscreen1 on SD/-his, replica plating onto SD/-his containing 1 mg/ml 5-fluoroorotic acid (5-FOA, Sigma) and 20 g/l galactose. These conditions select for the loss of the KRE9 wild-type expressed from the PRS316 and induces the KNH1 gene which functionally substitutes for the KRE9 gene. Colonies that grew on these plates were replica plated onto SD/-his plus galactose and SD/-his/-ura plus glucose. Colonies which grow on SD/-his plus galactose and fail to grow on SD/-his/-ura plus glucose are presumed to have lost the PRS 316-KRE9 containing plasmid. A strain isolated in this way was designated Yscreen2. Saturated liquid cultures from a single colony were placed at −80° C. in 25% glycerol for long term storage.

Other disrupted strains of KRE9 that can be used in the invention can be constructed using methods known in the art (Baudin et al., 1994, Nuc. Acids Res. 21:3329–3330; Guthrie and Fink supra; Wach et al., 1994, Yeast 10:1793–1808).
Step 2: Plasmid Constructs The plasmid vector used in the screen was constructed as follows. pACT2, a commercially available yeast expression vector (Clontech), was digested with Sma I and then partially digested with Hind III to remove a 491 bp fragment containing the gal4 activation domain. The Hind III ends were blunted with T4 DNA polymerase and the vector was religated using T4 DNA ligase. This vector designated pACT2-ΔH3/Sma.

The KRE9 gene was amplified out of *S. cerevisiae* using gene-specific primers by PCR. For wild type KRE9 the 5' primer was 5'-CTCGAGCTCAGAGAATCAGCAACTGTGA-3' (SEQ ID NO:7) and the 3' primer was 5'-AGATCTTCATACTTTTCTCATGTTGATTTTCC-3' (SEQ ID NO:8). The resulting product has an Xho I site at the 5' end and a Bgl II site at the 3' end. This insert was cloned into pCR2.1 (Invitrogen; San Diego, Calif.). Individual colonies were sequenced to verify identity, digested with Xho I and Bgl II, and the KRE9 sequence ligated into pACT2-ΔH3/Sma to create pACT2-KRE9.

Figure 1A:
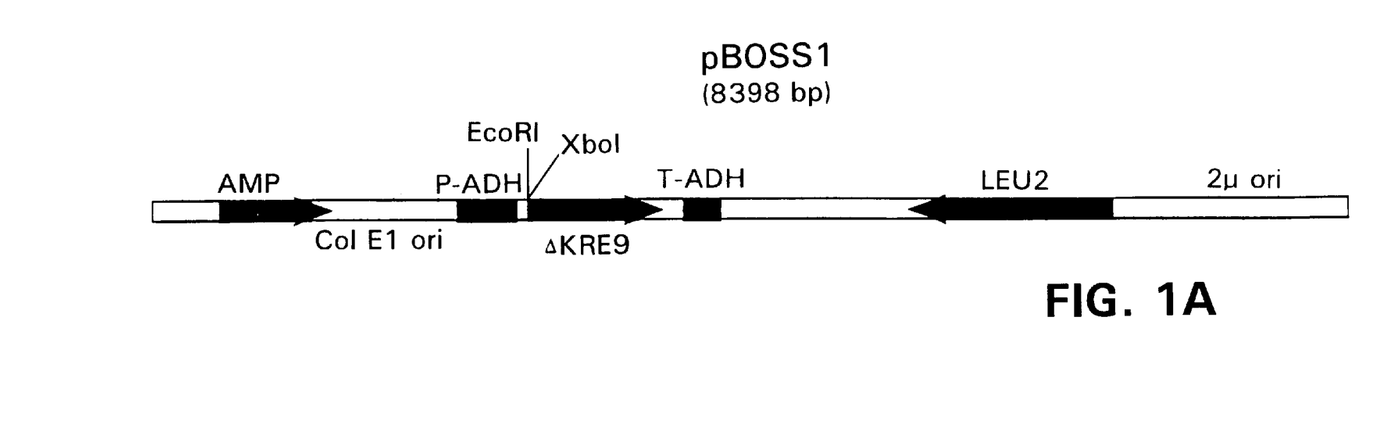
FIG. 1A is an illustration of the vector pBOSS1.

To generate a vector to be used for library construction, a similar vector was prepared containing a KRE9 cDNA lacking the first 66 nucleotides of KRE9 (ΔKRE9). These 66 nucleotides encode 22 amino acids of a region which includes the translation initiation and predicted signal peptide. Vector ΔKRE9 was amplified by PCR using the forward primer 5'-CTCGAGGTGAATATTGTTTCCCCCAGCTC-3' (SEQ ID NO:9) and the same 3' primer as previously. This insert was cloned into pACT2-ΔH3/Sma to make pBOSS1 (FIG. 1A). A third form of KRE9 (ΔKRE9met) containing an initiating methionine codon but lacking a signal peptide was prepared in a similar manner, using the forward primer 5'-CTCGAGGATAATGGTGAATATTGTTTCCCCCAGC-TC-3' (SEQ ID NO:10) in combination with the same 3' primer as before. The resulting cDNA was ligated into pACT2-ΔH3/Sma generating pACT2-ΔKRE9met. Finally, a DNA fragment encoding the first 31 amino acids of human placental alkaline phosphatase (Genbank accession no. M13078; Millan, 1986, J. Biol. Chem. 261:3112–3115, published erratum appears in J. Biol. Chem. 1991, 266:4023), including signal sequence, was ligated in-frame to pBOSS1 as an EcoR I/Xho I fragment to generate a plasmid termed pBOSS-AP.

Step 3: Library Construction cDNA for ligation to pBOSS1 was prepared from poly A+ RNA isolated from human osteoblasts by a modification of a commercially available cDNA synthesis kit (Stratagene: ZAP cDNA synthesis kit, catalog #200401). Single-stranded cDNA was synthesized from 5 µg of human osteoblast polyA+ RNA using the following random hexamer primer (SEQ ID NO:11) incorporating an Xho I restriction site (underlined).

5'-CTGA<u>CTCGAG</u>NNNNNN-3' (SEQ ID NO:11)

To generate short cDNA fragments, some of which would be expected to represent the 5' ends of mRNAs that contain signal sequences, random priming was employed rather than the oligo d(T) priming method suggested by Stratagene. The single-stranded cDNA was made double-stranded, DNA linkers containing a fire EcoR I overhang were ligated to both ends of the double-stranded cDNAs, and the linker-adapted double-stranded cDNAs were then digested with Xho I to generate a free Xho I overhang at the 3' ends of the cDNAs. All steps were performed using reagents from the Stratagene ZAP cDNA synthesis kit according to the manufacturer's instructions. Linker-adapted double-stranded cDNAs were size selected by gel filtration through SEPHACRYL® brand S-500 cDNA Size Fractionation Columns (Gibco BRL; Bethesda, Md.: Catalog #18092-015) according to the manufacturer's instructions.

Size selected, double-stranded cDNAs were ligated to pBOSS1 which had been digested with EcoR1 and Xho1 and purified by agarose gel electrophoresis. Following overnight incubation at 16° C., the ligation reactions were extracted with phenol/chloroform and precipitated with three volumes of absolute ethanol. Following centrifugation and extensive washing with 70% ethanol, the precipitate was resuspended in 5 µl water, and 1 µl of the suspension was used to transform electrocompetent DH10B E. coli (Gibco BRL) according to manufacturer's instructions using a Bio-Rad electroporation apparatus. The transformation was titered by plating dilutions of electroporated bacteria on LB plates containing 100 µg/ml ampicillin. Once titered, the entire library was transformed, plated onto LB-ampicillin plates, and grown overnight at 37° C. The following day, bacteria growing on the plates were scraped into LB, and plasmid DNA was prepared using Qiagen MEGA COLUMNS® brand spin columns, following manufacturer's instructions (Qiagen; Santa Clarita, Calif.). DNA was quantitated spectrophotometrically and analyzed by agarose gel electrophoresis.

Step 4: Yeast Transformation

Figure 1B:
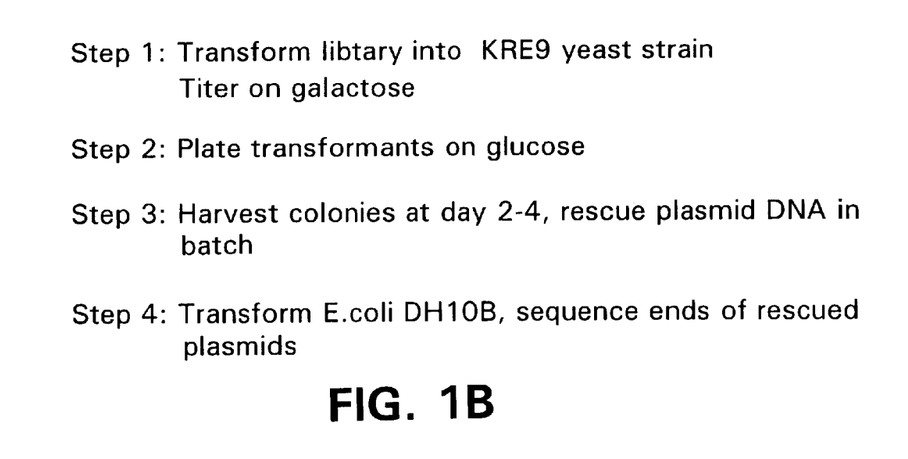
FIG. 1B lists key steps in the identification of cDNAs containing signal peptide encoding sequences.

To select and identify plasmids containing signal sequences (FIG. 1B), a single colony of yeast strain Yscreen2 was inoculated into 50 ml of SC/-his/2% galactose and grown to saturation at 30° C. with shaking. This culture was diluted to an $OD_{600nm}$ of 0.3 with fresh SC/-his/2% galactose, grown for approximately four hours to an $OD_{600nm}$ of 0.8. The cells were collected by centrifugation, washed once with water, and resuspended in 1.5 ml TE/LiAc (10 mM Tris pH 8; 1 mM EDTA/100 mM lithium acetate). To 50 µg of library DNA (see Example 3), 2 mg sonicated herring testes DNA (Clontech: catalog #S0277; prepared by boiling for 20 minutes and placing on ice for 5 minutes) and 1 ml Yscreen2 (prepared as above) were added to a 50 ml conical tube. Six milliliters of PEG/LiAc (40% polyethylene glycol; LiAc (10 mM TRIS pH 8; 1 mM EDTA/100 mM lithium acetate) were added to tube and vortexed to mix. The mixture was incubated at 300° C. for 30 minutes with shaking. Seventy microliters of dimethylsulfoxide was added, the cells gently inverted to mix, and then heat shocked for 15 minutes at 42° C., with occasional swirling. Cells were pelleted, chilled on ice, and resuspended in 2.5 ml TE (10 mM TRIS pH 8; 1 mM EDTA). Next, 250 µl of cells was plated onto each of ten 15-cm plates containing selection media (SC/-his/-leu/2% glucose). Omitting histidine from growth plates maintains selection for disruption of the endogenous KRE9 gene. Omitting leucine selects for the pBOSS1 library plasmid, and the presence of glucose ensures that growth will be seen only in those cells having a functional signal peptide fused to the KRE9 polypeptide.

Plates were incubated for 2–4 days at 30° C. or until colonies were apparent. Colonies were scraped from plates resuspended in 5 ml of YPD, and pooled in a 50 ml conical tube. Next, the cells were pelleted, washed once with water, and resuspended in 1 ml yeast lysis buffer. An equal volume of phenol:chloroform:isoamyl alcohol (25:24:1) and washed glass beads were added to tube containing yeast cells. The mixture was vortexed vigorously for two minutes, spun in an Eppendorf microcentrifuge for 5 minutes, and the supernatant was transferred to a clean tube. To 40 µl DH10B electrocompetent cells, 0.5 µl of supernatant (as prepared above) was added, and mixed on ice. Cells were electroporated using a Bio-Rad GENE PULSER II® brand electroporation system. One pulse was delivered at 2.5 kv, 25 µ3, 100Ω in a disposable electroporation cuvette with a 0.1 cm gap (Bio-Rad; #165-2089). Following electroporation, 1 ml SOC was added, and the mixture was incubated with shaking at 30° C. for 1 hour. Bacteria were plated on LB-ampicillin plates and incubated overnight at 37° C. The next day, individual colonies were inoculated into 1 ml of LB-ampicillin culture medium in 96-well plates and grown overnight with shaking. One hundred microliter samples were transferred to a new 96-well plate containing 100 µl 50% glycerol per well, and stored at −80° C. A portion of glycerol stock was used to inoculate fresh LB-ampicillin cultures. Following overnight growth, an AGTC (Advanced Genetic Technology Corporation; Gaithersberg, Md.) plasmid preparation was performed and the plasmids isolated from each culture were sequenced from both ends to determine the presence and nature of inserts. The forward sequencing primer was 5'-GAGCAACGGTATACGGCCTCCTT-3' (SEQ ID NO:12), and the reverse sequencing primer was 5'-GGGATATGCCCCATTATCCATC-3' (SEQ ID NO:13).

Example 2

KRE9 Requires its Signal Sequence to Function and a Heterologous Mammalian Signal Peptide can Restore Function to KRE9 Lacking its Native Signal Sequence Various test constructs were used to transform the KRE9 null mutant strain (Yscreen2). Expression vectors containing KRE9 with its signal sequence removed (pACT-ΔKRE9), or containing KRE9 with its signal sequence removed but with a translation initiating methionine added (pACT-ΔKRE9met) were unable to rescue the growth of the KRE9 null mutant on glucose. Thus, cells expressing non-secretable KRE9 behave as null mutants. In contrast, a vector containing a form of KRE9 in which the native signal peptide was replaced with the signal peptide of human placental alkaline phosphatase (pBOSS-AP) did restore growth on glucose. These results indicate that KRE9 requires its signal sequence to function, and that heterologous mammalian signal peptides are able to substitute for the native KRE9 signal peptide. Thus, restoration of function of an episomal non-secretable KRE9 gene can serve as the basis for a screen for novel mammalian signal peptides in yeast.

Example 3

Screening of a Human Osteoblast cDNA Library Identifies Novel Signal Peptides To identify novel mammalian signal peptides, a human osteoblast cDNA library was prepared in pBOSS1 and transformed into the yeast strain Yscreen2 as described above. cDNA inserts of plasmids rescued from the resulting yeast colonies after selection on glucose were sequenced. Of the novel signal peptides identified, two are represented in FIGS. 2 and 3.

Figure 2:
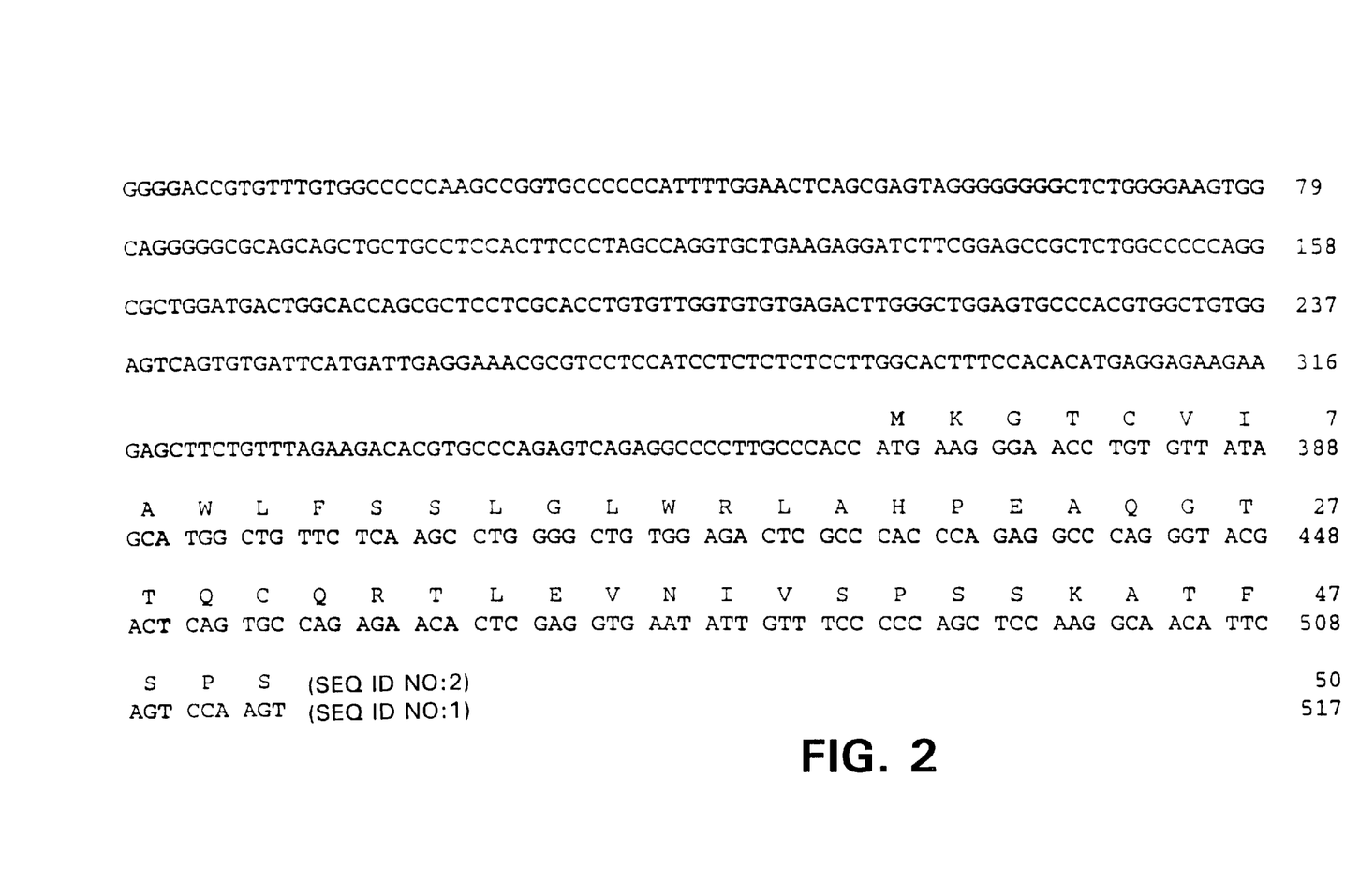
FIG. 2 illustrates the nucleic acid sequence (SEQ ID NO:1) and deduced amino acid sequence (SEQ ID NO:2) of emxosb4a11.
Figure 3:
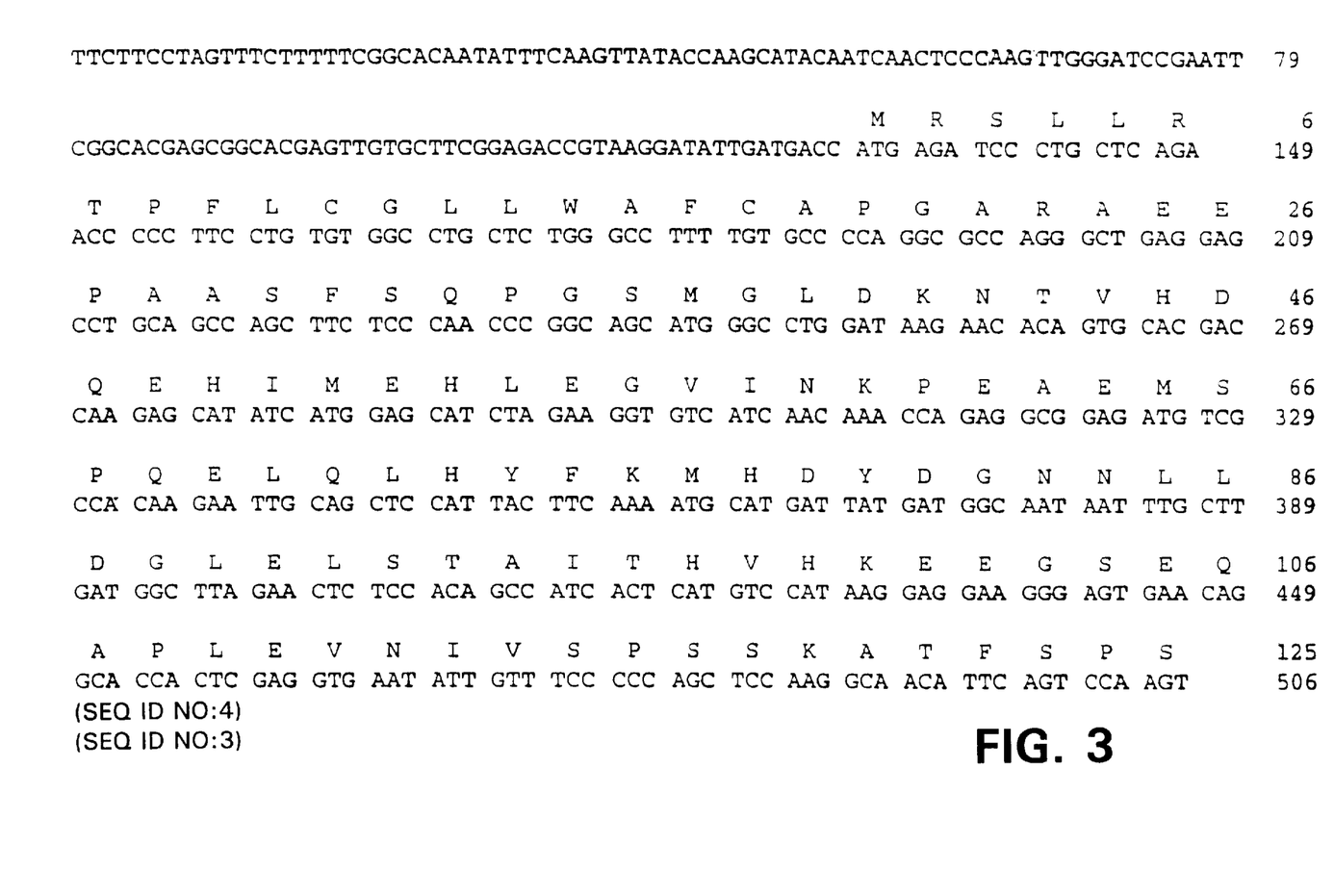
FIG. 3 illustrates the nucleic acid sequence (SEQ ID NO:3) and deduced amino acid sequence (SEQ ID NO:4) of emxosb4f08.
Figure 4:
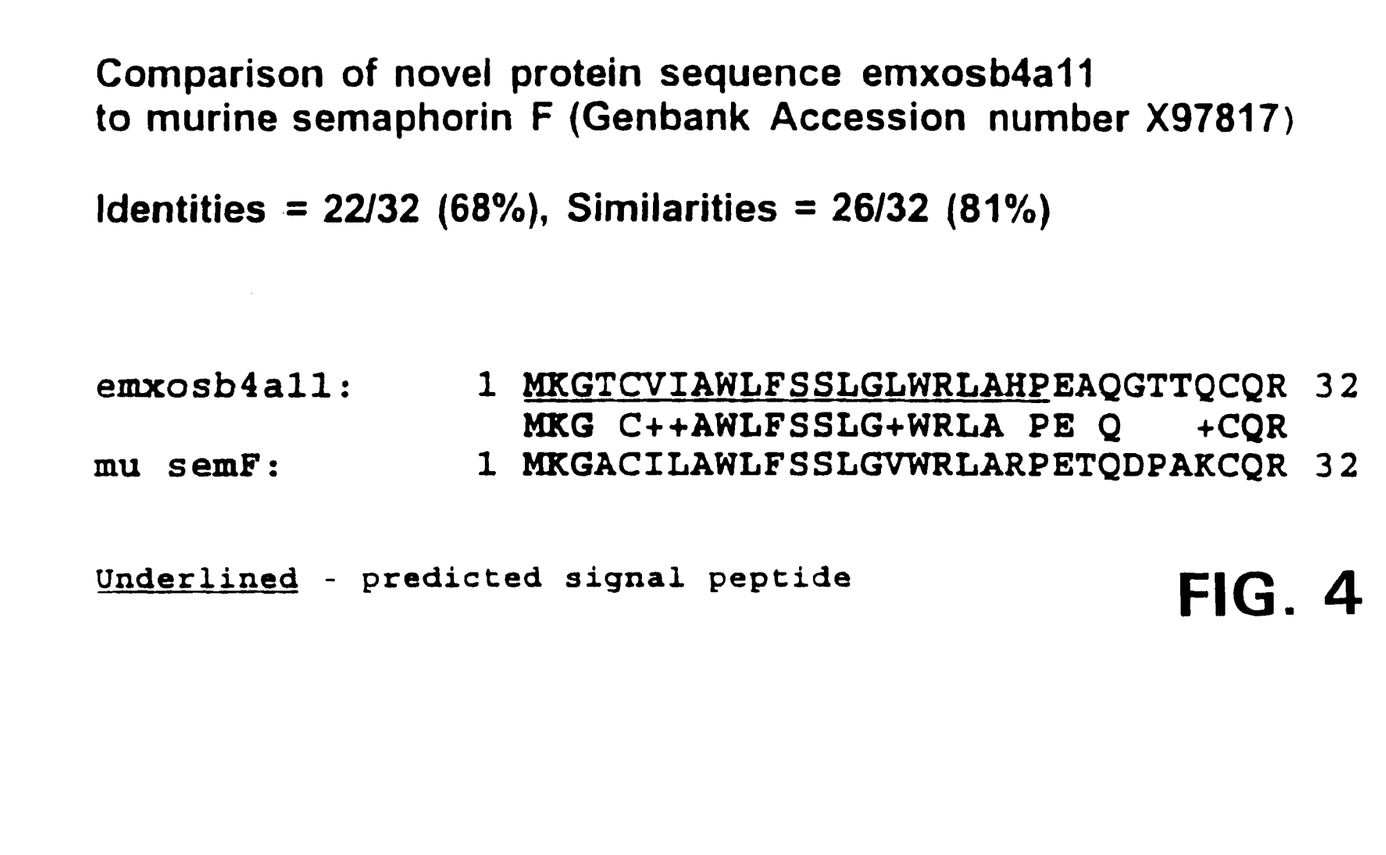
FIG. 4 illustrates the deduced amino acid sequence of emxosb4a11 (SEQ ID NO:2) and its alignment (SEQ ID NO:14) to a portion of murine semaphorin F (SEQ ID NO:5).

FIG. 4 shows a 32 amino acid open reading frame, translated from the novel sequence identified in the cDNA clone shown in FIG. 2, termed emxosb4all (SEQ ID NO:2) and its alignment (SEQ ID NO:14) with a protein known as semaphorin F (SEQ ID NO:5). The sequence displays 68% identity (i.e., the aligned amino acid sequences are identical) and 81% similarity (i.e., the aligned amino acids are identical or are conservative changes) to the amino terminal signal peptide of semaphorin F (Genbank accession number X97817). Analysis of the emxosb4all protein sequence with the signal peptide prediction algorithm, Signal P (Nielsen et al., 1997, supra), confirmed that a likely cleavage site between amino acids 22 (a proline) and 23 (a glutamic acid) exists in this novel clone. Thus, clone emxosb4all encodes the signal peptide of a novel protein related to semaphorin F.

Figure 5:
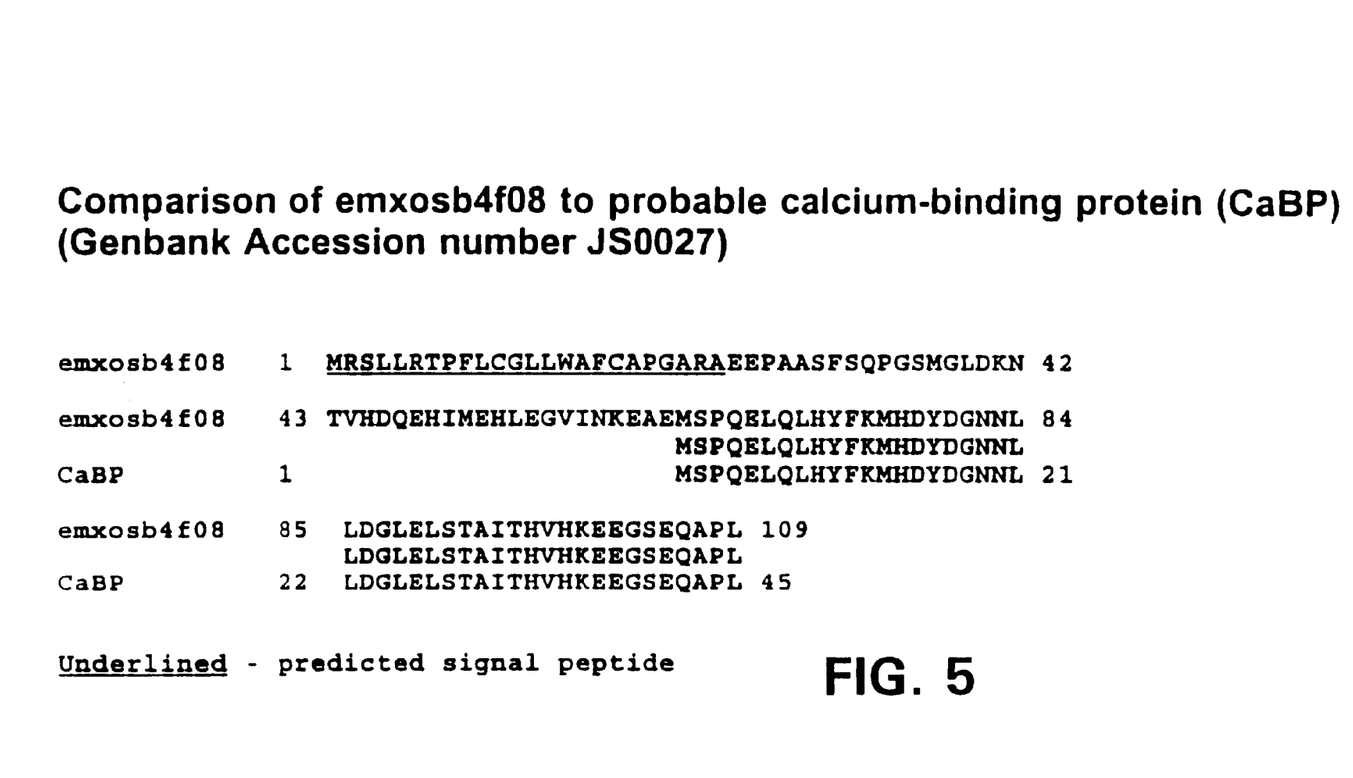
FIG. 5 illustrates the deduced amino acid sequence of emxosb4f08 (SEQ ID NO:4) and its alignment (SEQ ID NO:15) to a portion of a putative calcium binding protein (SEQ ID NO:6).

FIG. 5 shows a 108 amino acid open reading frame translated from the cDNA clone (FIG. 3) termed emxosb4f08 (SEQ ID NO:4), which from amino acid 64 displays complete identity (SEQ ID NO:15) to the amino terminal region of a putative calcium binding protein (SEQ ID NO:6) (Genbank accession number JS0027). Upstream of amino acid 64, however, the emxosb4f08 open reading frame extends to an initiating methionine which is followed by a stretch of hydrophobic residues characteristic of a signal peptide. Analysis of this sequence with Signal P (Nielsen et al., 1997, supra) confirmed the presence of a signal peptide in this sequence, with a likely cleavage site between amino acids 24 (an alanine) and 25 (a proline). Thus, emxosb4f08 encodes a novel form of this calcium binding protein which contains a signal sequence.

Example 4

Selection Using K1 Killer Toxin

KRE9 null mutants are resistant to the K1 killer toxin (Brown and Bussey, 1993). The restoration of function of non-secretable KRE9 by heterologous signal sequences will restore toxin sensitivity. Thus, screening for colonies sensitive to K1 killer toxin offers a semiquantitative assay for KRE9 function.

K1 killer toxin is prepared using strain T158C/S14a as described (Bussey et al., 1983, Mol. Cell. Biol 3:1362–1370). Leu$^+$ transformants containing library plasmids are tested by a zone of inhibition assay. For each strain, 0.1 ml of cell suspension (1×10$^7$ cells/ml water) is added to 10 ml of molten medium (e.g., 1% agar cooled to 45° C. containing either 1×Halverson's buffered YEPD, pH4.7, or minimal medium, pH4.7). The agar-cell suspension is immediately poured into petri plates. Concentrated toxin is spotted on the surface of the solidified agar-cell suspension, and the plate is incubated overnight at 18° C. followed by 24 hours at 30° C. Sensitive strains display a zone of inhibition; the diameter of the zone is proportional to KRE9 activity. Thus, resistant clones are eliminated from further consideration while sensitive clones are prioritized by the diameter of the zone of inhibition.

Example 5

Selection in the Presence of Calcineurin Inhibition

KRE9 null mutants are hypersensitive to inhibitors of the protein phosphatase calcineurin. This is because KNH1, which can functionally replace KRE9 when induced by galactose, is positively regulated by calcineurin. Thus, calcineurin inhibitors, such as cyclosporin A and FK506, are expected to further suppress the KNH1 pathway on glucose-containing media, thereby increasing the likelihood that clones growing on glucose contain a functional KRE9 chimera.

To use calcineurin in the selection of functional KRE9 chimeras, the growth of a Leu$^+$ transformant containing a library plasmid is compared to the growth of a control strain (e.g., Yscreen containing pACT2-KRE9) on solid medium (e.g., SD or YPD) containing a gradient either FK506 (from 0 to 5 μg/ml) or cyclosporin A (from 0 to 100 μg/ml). Those strains that are as resistant to FK506 and/or cyclosporin A as the control strain are prioritized for further analysis.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 15

<210> SEQ ID NO 1
<211> LENGTH: 517
<212> TYPE: DNA
<213> ORGANISM: Homo sapiens
<220> FEATURE:
<221> NAME/KEY: CDS
<222> LOCATION: (368)...(517)

<400> SEQUENCE: 1
ggggaccgtg tttgtggccc ccaagccggt gcccccatt ttggaactca gcgagtaggg      60
ggcggctctg gggaagtggc aggggcgca gcagctgctg cctccacttc cctagccagg     120
```

```
tgctgaagag gatcttcgga gccgctctgg cccccaggcg ctggatgact ggcaccagcg    180
ctcctcgcac ctgtgttggt gtgtgagact tgggctggag tgcccacgtg gctgtggagt    240
cagtgtgatt catgattgag gaaacgcgtc ctccatcctc tctctccttg cactttcca     300 cacatgagga gaagaagagc ttctgtttag aagacacgtg cccagagtca gaggcccctt    360 gcccacc atg aag gga acc tgt gtt ata gca tgg ctg ttc tca agc ctg     409
        Met Lys Gly Thr Cys Val Ile Ala Trp Leu Phe Ser Ser Leu
          1               5                  10 ggg ctg tgg aga ctc gcc cac cca gag gcc cag ggt acg act cag tgc     457
Gly Leu Trp Arg Leu Ala His Pro Glu Ala Gln Gly Thr Thr Gln Cys
 15              20                  25                  30 cag aga aca ctc gag gtg aat att gtt tcc ccc agc tcc aag gca aca     505
Gln Arg Thr Leu Glu Val Asn Ile Val Ser Pro Ser Ser Lys Ala Thr
                 35                  40                  45 ttc agt cca agt                                                      517
Phe Ser Pro Ser
         50

<210> SEQ ID NO 2
<211> LENGTH: 50
<212> TYPE: PRT
<213> ORGANISM: Homo sapiens

<400> SEQUENCE: 2

Met Lys Gly Thr Cys Val Ile Ala Trp Leu Phe Ser Ser Leu Gly Leu
  1               5                  10                  15

Trp Arg Leu Ala His Pro Glu Ala Gln Gly Thr Thr Gln Cys Gln Arg
                 20                  25                  30

Thr Leu Glu Val Asn Ile Val Ser Pro Ser Ser Lys Ala Thr Phe Ser
             35                  40                  45

Pro Ser
     50

<210> SEQ ID NO 3
<211> LENGTH: 506
<212> TYPE: DNA
<213> ORGANISM: Homo sapiens
<220> FEATURE:
<221> NAME/KEY: CDS
<222> LOCATION: (132)...(506)

<400> SEQUENCE: 3
ttcttcctag tttcttttc ggcacaatat ttcaagttat accaagcata caatcaactc     60 ccaagtggg atccgaattc ggcacgagcg gcacgagttg tgcttcggag accgtaagga    120
tattgatgac c atg aga tcc ctg ctc aga acc ccc ttc ctg tgt ggc ctg    170
            Met Arg Ser Leu Leu Arg Thr Pro Phe Leu Cys Gly Leu
              1               5                  10 ctc tgg gcc ttt tgt gcc cca ggc gcc agg gct gag gag cct gca gcc    218
Leu Trp Ala Phe Cys Ala Pro Gly Ala Arg Ala Glu Glu Pro Ala Ala
 15              20                  25 agc ttc tcc caa ccc ggc agc atg ggc ctg gat aag aac aca gtg cac    266
Ser Phe Ser Gln Pro Gly Ser Met Gly Leu Asp Lys Asn Thr Val His
 30              35                  40                  45 gac caa gag cat atc atg gag cat cta gaa ggt gtc atc aac aaa cca    314
Asp Gln Glu His Ile Met Glu His Leu Glu Gly Val Ile Asn Lys Pro
                 50                  55                  60 gag gcg gag atg tcg cca caa gaa ttg cag ctc cat tac ttc aaa atg    362
Glu Ala Glu Met Ser Pro Gln Glu Leu Gln Leu His Tyr Phe Lys Met
 65                  70                  75
```

```
cat gat tat gat ggc aat aat ttg ctt gat ggc tta gaa ctc tcc aca      410
His Asp Tyr Asp Gly Asn Asn Leu Leu Asp Gly Leu Glu Leu Ser Thr
             80                  85                  90 gcc atc act cat gtc cat aag gag gaa ggg agt gaa cag gca cca ctc      458
Ala Ile Thr His Val His Lys Glu Glu Gly Ser Glu Gln Ala Pro Leu
     95                 100                 105 gag gtg aat att gtt tcc ccc agc tcc aag gca aca ttc agt cca agt      506
Glu Val Asn Ile Val Ser Pro Ser Ser Lys Ala Thr Phe Ser Pro Ser
110             115                 120                 125
```

<210> SEQ ID NO 4
<211> LENGTH: 125
<212> TYPE: PRT
<213> ORGANISM: Homo sapiens

<400> SEQUENCE: 4

```
Met Arg Ser Leu Leu Arg Thr Pro Phe Leu Cys Gly Leu Leu Trp Ala
 1               5                  10                  15

Phe Cys Ala Pro Gly Ala Arg Ala Glu Glu Pro Ala Ala Ser Phe Ser
                20                  25                  30

Gln Pro Gly Ser Met Gly Leu Asp Lys Asn Thr Val His Asp Gln Glu
        35                  40                  45

His Ile Met Glu His Leu Glu Gly Val Ile Asn Lys Pro Glu Ala Glu
 50                  55                  60

Met Ser Pro Gln Glu Leu Gln Leu His Tyr Phe Lys Met His Asp Tyr
65                  70                  75                  80

Asp Gly Asn Asn Leu Leu Asp Gly Leu Glu Leu Ser Thr Ala Ile Thr
                85                  90                  95

His Val His Lys Glu Glu Gly Ser Glu Gln Ala Pro Leu Glu Val Asn
                100                 105                 110

Ile Val Ser Pro Ser Ser Lys Ala Thr Phe Ser Pro Ser
        115                 120                 125
```

<210> SEQ ID NO 5
<211> LENGTH: 32
<212> TYPE: PRT
<213> ORGANISM: Mus musculus

<400> SEQUENCE: 5

```
Met Lys Gly Ala Cys Ile Leu Ala Trp Leu Phe Ser Ser Leu Gly Val
 1               5                  10                  15

Trp Arg Leu Ala Arg Pro Glu Thr Gln Asp Pro Ala Lys Cys Gln Arg
                20                  25                  30
```

<210> SEQ ID NO 6
<211> LENGTH: 45
<212> TYPE: PRT
<213> ORGANISM: Homo sapiens

<400> SEQUENCE: 6

```
Met Ser Pro Gln Glu Leu Gln Leu His Tyr Phe Lys Met His Asp Tyr
 1               5                  10                  15

Asp Gly Asn Asn Leu Leu Asp Gly Leu Glu Leu Ser Thr Ala Ile Thr
                20                  25                  30

His Val His Lys Glu Glu Gly Ser Glu Gln Ala Pro Leu
        35                  40                  45
```

<210> SEQ ID NO 7
<211> LENGTH: 28

```
<212> TYPE: DNA
<213> ORGANISM: Artificial Sequence
<220> FEATURE:
<223> OTHER INFORMATION: primer

<400> SEQUENCE: 7
ctcgagctca gagaatcagc aactgtga                                              28

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
agatcttcat acttttctca tgttgatttt cc                                         32

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
ctcgaggtga atattgtttc ccccagctc                                             29

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
ctcgaggata atggtgaata ttgtttcccc cagctc                                     36

<210> SEQ ID NO 11
<211> LENGTH: 16
<212> TYPE: DNA
<213> ORGANISM: Artificial Sequence
<220> FEATURE:
<221> NAME/KEY: primer
<222> LOCATION: (11)...(16)
<223> OTHER INFORMATION: where "n" at positions 11-16 is any one of
      A, T, G, or C

<400> SEQUENCE: 11
ctgactcgag nnnnnn                                                           16

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
gagcaacggt atacggcctt cctt                                                  24

<210> SEQ ID NO 13
<211> LENGTH: 22
<212> TYPE: DNA
<213> ORGANISM: Artificial Sequence
<220> FEATURE:
<223> OTHER INFORMATION: primer
```

```
<400> SEQUENCE: 13
gggatatgcc ccattatcca tc                                              22

<210> SEQ ID NO 14
<211> LENGTH: 32
<212> TYPE: PRT
<213> ORGANISM: Homo sapiens

<400> SEQUENCE: 14

Met Lys Gly Thr Cys Val Ile Ala Trp Leu Phe Ser Ser Leu Gly Leu
  1               5                  10                  15

Trp Arg Leu Ala His Pro Glu Ala Gln Gly Thr Thr Gln Cys Gln Arg
             20                  25                  30

<210> SEQ ID NO 15
<211> LENGTH: 108
<212> TYPE: PRT
<213> ORGANISM: Homo sapiens

<400> SEQUENCE: 15

Met Arg Ser Leu Leu Arg Thr Pro Phe Leu Cys Gly Leu Leu Trp Ala
  1               5                  10                  15

Phe Cys Ala Pro Gly Ala Arg Ala Glu Glu Pro Ala Ala Ser Phe Ser
             20                  25                  30

Gln Pro Gly Ser Met Gly Leu Asp Lys Asn Thr Val His Asp Gln Glu
         35                  40                  45

His Ile Met Glu His Leu Glu Gly Val Ile Asn Lys Glu Ala Glu Met
     50                  55                  60

Ser Pro Gln Glu Leu Gln Leu His Tyr Phe Lys Met His Asp Tyr Asp
 65                  70                  75                  80

Gly Asn Asn Leu Leu Asp Gly Leu Glu Leu Ser Thr Ala Ile Thr His
                 85                  90                  95

Val His Lys Glu Glu Gly Ser Glu Gln Ala Pro Leu
                100                 105
```

What is claimed is:

1. An isolated nucleic acid molecule comprising a nucleotide sequence which encodes a polypeptide comprising the amino acid sequence of SEQ ID NO:2 or 4.

2. An isolated nucleic acid molecule comprising the nucleotide sequence of SEQ ID NO:1 or 3.

3. An isolated nucleic acid molecule comprising the open reading frame of the nucleotide sequence of SEQ ID NO:1 or 3.

4. The nucleic acid molecule as in any one of claims 1 to 3 further comprising nucleic acid sequences encoding polypeptide which is heterologous to a polypeptide encoded by the nucleic acid molecule as in any one of claims 1 to 3.

5. A vector comprising the nucleic acid molecule of claim 4 which further comprises nucleic acid sequence encoding a polypeptide which is heterologous to a polypeptide encoded by the nucleic acid molecule of claim 4.

6. A host cell which contains the vector of claim 5.

7. The host cell of claim 6, which is a mammalian host cell.

8. A host cell comprising the nucleic acid molecule of claim 4 which further comprises nucleic acid sequences encoding a polypeptide which is heterologous to a polypeptide encoded by the nucleic acid molecule of claim 4.

9. The host cell of claim 8, which is mammalian host cell.

10. A vector comprising a nucleic acid molecule as in any of claim 1.

11. A host cell which contains the vector of claim 10.

12. The host cell of claim 11, which is a mammalian host cell.

13. A host cell which contains the nucleic acid molecule as in any one of claims 1 to 3.

14. The host cell of claim 13, which is a mammalian host cell.

* * * * *